United States Patent [19]

Chaleff

[11] 4,443,971
[45] Apr. 24, 1984

[54] HERBICIDE-TOLERANT PLANTS

[75] Inventor: Roy S. Chaleff, Ithaca, N.Y.

[73] Assignee: Cornell Research Foundation, Inc., Ithaca, N.Y.

[21] Appl. No.: 311,129

[22] Filed: Oct. 14, 1981

Related U.S. Application Data

[63] Continuation of Ser. No. 85,432, Oct. 16, 1979, abandoned.

[51] Int. Cl.$^3$ .............................................. A01G 1/00
[52] U.S. Cl. ........................................................ 47/58
[58] Field of Search ............................................ 47/58

[56] References Cited

PUBLICATIONS

Green et al., *Crop Science*, 15: 417–421 (1975).
Cummings et al., *Crop Science*, 16: 465–470 (1976).
Saunders et al., *Crop Science*, 12: 804–808 (1972).
McCoy et al., *Plant Science Letters*, 10: 59–66 (1977).
Steward et al., *Amer. J. Bot.*, 45: 705–713 (1958).
Shimada et al., *Japan. J. Genetics*, 54: 379–385 (1979).
Nishi et al., *Nature*, 219: 508–509 (1968).
Gamborg et al., *Plant Science Letters*, 10: 67–74 (1977).
Phillips et al., *Crop Science*, 19: 59–64 (1979).
Green, "*In Vitro* Plant Regeneration in Cereals and Grasses", from *Frontiers of Plant Tissue Culture 1978*, T. Thorpe, Ed., Pub. Intl. Assoc. for Plant Tissue Culture (1978) Proc. of Conf. held Aug. 20–25 (1978).
Shepard et al., *Plant Physiol.*, 60: 313–316 (1977).
Lam, *Amer. Potato Journal*, 54: 575–580 (1977).
Heinz et al., *Amer. J. Bot.*, 68: 257–262 (1971).
Heinz et al., *Crop Science*, 10: 696–699 (1970).
Nadar et al., *Crop Science*, 18: 210–216 (1978).
Green, *Proc. 5th Intl. Cong. Plant Tissue & Cell Culture*, 107–108.
Lee et al., *Theor. Appl. Genet.*, 62: 109–112 (1982).
Green et al., from "Maize for Biological Research", Sheridan, ed., Plant Molecular Biology Assn., 1982.
Bretell et al., *Theor. Appl. Genet.*, 58: 55–58 (1980).
Hibberd et al., *Proc. Natl. Acad. Sci. USA*, 79: 559–563 (1982).
Genetic Engineering Letter, Jun. 24, 1983.
Thomas et al., *Theor. Appl. Genet.*, 63: 169–176 (1982).
Yarkova et al., *Biochem. Physiol. Pflanzen*, 177: 337–344 (1982).
Ozias–Akins et al., *Protoplasma*, 110: 95–105 (1982).
Heyser et al., *Z. Pflanzenphysiol. Bd.*, 107S: 153–160 (1982).
Johnson et al., *Plant Science Letters*, 20: 297–304 (1981).
Gumm et al., *Plant Science Letters*, 22: 97–101 (1981).
Thomas, *Plant Science Letters*, 23: 81–88 (1981).
Vasil, *Proc. 5th Intl. Plant Tissue and Cell Culture*, 101–104.

*Primary Examiner*—Robert E. Bagwill

[57] ABSTRACT

This invention relates to herbicide-tolerant plants prepared by plant tissue culture. These plants are produced by culturing tissue of a plant sensitive to a particular herbicide in the presence of an amount of the herbicide, and for a time less than that sufficient to kill the entire plant-tissue population, but sufficient to kill a majority of the tissue population. If desired this procedure is repeated for sufficient passages, preferably with increasing amounts of said herbicide to provide a herbicide-tolerant strain of plant tissue which is subsequently subjected to differentiating growth conditions to provide herbicide-tolerant plants. In a preferred embodiment, plants, which display a heritable tolerance toward said herbicide as compared to the original plant, are selected from the whole population of tissue culture-derived plants. These plants can be propagated vegetatively using tissue culture methods to produce additional plants of the same genetic constitution. These plants also can be sexually reproduced to provide seeds and plants therefrom which display inherited tolerance to said herbicide.

11 Claims, No Drawings

HERBICIDE-TOLERANT PLANTS

This is a continuation of application Ser. No. 085,432, filed Oct. 16, 1979 now abandoned.

BACKGROUND OF THE INVENTION

A number of economically important plants are significantly sensitive to commercially utilized herbicides. These herbicides include herbicides which are or, absent adverse effects toward desired plant species, could be used to control weeds among a particular desireable plant stand; or herbicides which are known to damage a particular plant species, but come into contact with that plant species for example in run-off from an adjacent, different, non-sensitive plant stand which has been treated with the particular herbicide. At least one example of this latter problem is the damage done to alfalfa crops planted in proximity to corn crops when certain herbicides, commonly used to treat corn fields, accidently enter the alfalfa field.

DESCRIPTION OF THE INVENTION

This invention relates to a method of producing plants having increased tolerance to a particular herbicide, which broadly comprises culturing tissue of a plant sensitive to a particular herbicide in the presence of an amount of the herbicide, and for a time less than sufficient to kill the entire cultured plant tissue population, but sufficient to kill a majority of the tissue population, to isolate a herbicide tolerant strain of plant tissue, and then causing differentiating growth to provide a herbicide resistant plant.

Not all herbicides which kill or inhibit a growing plant will adversely affect a tissue culture of that plant. For example, herbicides which apparently function exclusively by interference with photosynthesis may not affect a tissue culture of that plant, since tissue culture growth does not rely on photosynthesis. Therefore, the herbicides which can be employed in the process of this invention are those herbicides to which both a tissue culture and the plant from which it was derived are both sensitive, i.e. a herbicide which in some manner interferes with a basic cellular metabolic process. The herbicides, useful herein, can be rapidly identified by screening them against a tissue culture of the plant which is known sensitive to the herbicide, and observing the presence or absence of an effect, as compared to a herbicide-free control culture.

Specific examples of herbicides which are useful in the process of the invention include picloram (Tordon), paraquat, 2,4-D, glyphosate (Roundup), alachlor (Lasso), cycloate, atrazine, and amitrole.

The plants whose tissue culture can be employed in this invention are virtually any plant economically important to man, tissues of which can be cultured and induced to form plants. Examples of such plants include tobacco (e.g. *Nicotiana tabacum*), rice (*Oryza sativa*), corn (*Zea mays*), potato (*Solanum tuberosum*), oats (*Avena sativa*), alfalfa (e.g. *Medicago sativa*), carrot (e.g. *Dancus carota*) and sugar cane (e.g. *Saccharum officinalis*).

The tissue culture system employed in the process of this invention can comprise any tissue culture medium capable of supporting tissue growth. Due to ease of manipulation, when suspension tissue culture can be used, a suspension tissue culture technique is the method of choice. Those skilled in the art are aware of the particular requirements to culture tissues of a particular plant species and to subsequently cause differentiating growth to form a plant therefrom. For a general discussion of tissue culture techniques attention is directed to "Plant Tissue and Cell Culture", H. E. Street ed., University of California Press (in two editions 1973, 1977).

It is noted that, for the purposes of this invention, the term "tissue culture" includes the culture of plant tissues, cells or protoplasts. Further, the cells, protoplasts, or tissues which can be employed in the process of the invention can have originated from explants of haploid as well as diploid plants. Still further, haploid tissue cultures can be obtained directly from immature pollen contained within anthers.

Accordingly, the term "culturing tissue" and similar terms encompass the propagation of tissue, cells or protoplasts by the herein described "tissue culture" process.

The method of the present invention is essentially characterized in that a normal or parent plant, sensitive to a particular herbicide, tissues of which (including a particular portion of the plants or seeds from the plant) can be tissue cultured and which herbicide is also capable of inhibiting said tissue culture, is cultured in (including on) a growth supporting tissue culture medium, in a manner known per se, except that a critical amount of the herbicide is introduced into the tissue culture system, so as to kill the vast majority of cultured plant tissue while allowing survival of a small, relatively herbicide tolerant, portion of the tissue population.

The procedure can be repeated one or more times by transferring the surviving tissue to a new herbicide containing medium to produce a final relatively herbicide tolerant tissue culture. Preferably at least 90 percent and most preferably well in excess of 99 percent of the tissue is killed in the course of each of the culturing steps employed wherein herbicide has been introduced.

As to the basic procedural manipulative techniques, including culture materials and procedures, these materials and procedures are considered within the skill of the art and thus the procedures and materials are not discussed or described in detail.

In the process of the invention the plant-derived tissue is cultured in a conventional manner with the exception that there is added to the medium an amount of herbicide as set forth above. The herbicide is usually added to the medium prior to or at the time the plant tissue to be cultured is added, although the herbicide can be added later, after growth has begun. In each instance of addition, the amount of herbicide to be added can be most readily determined by screening a series of cultures containing varying amounts of herbicides and selecting from that series, for subsequent passage or differentiation and growth, that culture which displays the desired amount of surviving tissue (i.e. tissue, cells or protoplast). If desired, once the appropriate concentration of herbicide is determined, additional quantities of cultured plant tissue can be transferred to medium containing this concentration of herbicide to isolate relatively herbicide-tolerant strains of tissue.

The relatively herbicide-tolerant plants of the invention have the same characteristics as the original herbicide sensitive plant, except that they are significantly more tolerant to the particular herbicide.

While in one aspect of the invention all the plants grown from the surviving tissues in the tissue culture are useful per se as being relatively herbicide-tolerant or at least containing a substantially higher proportion of herbicide-tolerant plants, than does a normal population, it is especially preferred to isolate from the plants derived from the surviving cultured tissue those plants which display a heritable resistance to the particular herbicide, that is those plants wherein resistance to the particular herbicide is expressed by the progeny resulting from a sexual cross involving said plant. The identification of those individual plants which possess heritable herbicide tolerance may be accomplished in a number of ways. For example, tissue cultures derived from survivor tissue-derived plants can be screened for tolerance to the particular herbicide. Alternatively, seed produced by self fertilization or a cross of the survivor tissue-derived plants can be germinated and grown and the resultant plants tested for tolerance to the particular herbicide. Yet another method comprises germinating seed of a survivor tissue-derived plant in a medium or solution containing a predetermined amount of the particular herbicide. By any of these processes a plant displaying heritable herbicide-tolerance to the particular herbicide is isolated.

In the process of the invention, if desired, prior to exposure of the cultured tissue to the critical amount of the particular herbicide, the number of possible herbicide-tolerant cells (including protoplasts) present in the cultured tissue can be enhanced by treating the plant from which the cultured tissue is to be derived, or the cultured tissue, with a known mutagen, for example, chemicals, such as ethyl methane sulfonate or nitrosoguanidine, or radiation such as X-rays. Such plant mutation techniques are known in the art.

Further, if desired, differentiation of the survivor tissue to form plants can be enhanced by use of materials, for example, hormones such as auxins or cytokinins in a manner known in the art.

There follows an Example which is to be considered illustrative rather than limiting. All parts and percentages are by weight unless otherwise specified. All temperatures are degrees Centigrade unless otherwise specified.

EXAMPLE

In this example cultured cells of *Nicotiana tabacum* are exposed to the herbicide picloram (4-amino-3,5,6-trichloropicolinic acid) to obtain plants displaying heritable increased tolerance to picloram.

Plant material and conditions of culture: Seed of *Nicotiana tabacum* L. cv. Xanthi (obtained from the Connecticut Agricultural Experiment Station; New Haven, CT) were surface-sterilized by immersion for 15 minutes in a solution of 10% Clorox and 0.1% sodium lauryl sulfate. After being rinsed thoroughly with sterile distilled water, seed were germinated on a Linsamaier and Skoog medium containing 2% sucrose, 0.8% agar, and no hormones. (Linsmaier et al., Physiol. Plant., 18:100–127(1965)). Plants were grown aseptically on 50 ml of this same medium in a 250 ml flask. All media contained this same basic formulation, but differed in sucrose concentration and hormone composition. Callus cultures were initiated by macerating leaves from sterile plants on a medium supplemented with 3% sucrose, 2.0 mg α-naphthalene acetic acid (NAA) and 0.3 mg kinetin per liter (Cl). Cl medium also was used for maintenance of callus and suspension (agar omitted) cultures. Shoot formation was induced by transferring callus to an agar medium containing 3% sucrose and 0.3 mg indole-3-acetic acid (IAA) and 3.0 mg 6 (γ, γ-dimenthylallylamino)-purine (2iP) per liter (shoot-induction medium). Shoot formation usually required several passages (three weeks per passage) on this medium. Root formation was accomplished on a medium containing 3% sucrose and supplemented with 0.1 mg NAA/l. Plantlets were grown to a height of 5–8 cm on a hormone-free medium containing 1% sucrose before transfer to soil.

Concentrated aqueous solutions of picloram, IAA, and NAA were adjusted to pH 6.0 with KOH. Kinetin and 2iP were dissolved in 0.1 N KOH. Picloram and hormone solutions were sterilized by filtration and added to autoclaved medium.

Cell plating and mutant selection: Suspension cultures were filtered through cheesecloth and the filtrate was centrifuged for 10 minutes at 800 rpm. The supernatant then was decanted and the cells resuspended in an equal volume of fresh Cl liquid medium. Suspensions formed from several similar cultures were pooled and 2 ml of this suspension was pipetted into each petri dish (9 cm) containing either Cl medium (control) or Cl medium supplemented with 500 μM picloram (selective medium). Plates were sealed with parafilm and incubated at 25±1° C. under Gro-lux fluorescent lamps (16 h day). Resistant calluses appeared between 1 and 2 months later. Calluses which continued to grow during a second passage on selective medium were transferred to shoot-induction medium.

Scoring of crosses: Seed were surface-sterilized and plated on control (2% sucrose without hormones) and selective (supplemented with 100 μM picloram) media. In all crosses germination exceeded 99%. Normal seed germinated on selective medium, but development was severely inhibited. After 14 days seedlings were stunted, swollen, and bleached. Although resistant seedlings did not grow as well on selective as on control medium, they could be distinguished readily from sensitive seedlings on selective medium by formation of roots and greening of the cotyledons.

Growth tests: Suspension cultures were not used for growth tests because of the altered growth habit of callus derived from mutant plants and the effects of picloram on this growth habit. When grown on unsupplemented Cl medium, mutant callus is less friable than normal callus, but becomes progressively more friable on media containing increasing concentrations of picloram. Since it was expected that the degree of dispersion of the cells would influence the growth rate of suspension cultures, growth tests were performed on callus cultures. These callus cultures were obtained from $F_1$ plants produced by the selfing of PmR1/+ (the plant regenerated from the originally selected mutant cell line). Cultures used as a source of inocula were initiated and maintained on unsupplemented Cl medium and transferred to fresh medium three days prior to initiation of the growth tests. A concentrated picloram solution was diluted serially, filter-sterilized, and added to Cl medium containing 0.6% agar. A sterile 5.5 cm diameter filter disc (Whatman No. 1) was placed on the surface of the medium in each petri dish and approximately 50 mg tissue was spread on the filter. After two weeks at 25±1° C. the filter was transferred to a Buchner funnel and rinsed thoroughly with distilled water. The callus then was scraped from the surface of the filter and weighed.

Nomenclature of crosses: The term $F_1$ has been used herein to designate progeny resulting from the first cross of a heterozygous mutant plant regenerated from cell culture. As this term usually refers to heterozygous progeny produced by crossing two homozygous parents, the authors recognize that to many this usage may seem inappropiate and even confusing. This difficulty makes apparent the need for defining a new terminology to describe a heterozygous plant regenerated from culture and its progeny. However, until general discussion and agreement on the introduction of new terminology, we have opted for the familiar nomenclature employed herein.

RESULTS

Mutation frequency: Several features of the growth of plant cells in culture make it difficult to estimate the frequency of spontaneous mutation from picloram sensitivity to picloram resistance. Cultured tobacco cells grow as aggregates and even following filtration through cheesecloth the number of cells per aggregate is too large to permit an accurate count of the initial cell number to be made. In addition, because growth of nonmutant cells is impaired greatly, but not completely by 500 μM picloram (Table 1), mutants appear at a total frequency that is the sum of the mutation frequency (mutations present in the initial cell population) and rate (mutations occurring per generation). Furthermore, without a genetic analysis of regenerated plants the number of resistant cell lines that are true mutants is not known. Also unknown is the number of loci at which mutations can produce the resistance phenotype.

In one experiment the approximate size of the initial cell population was determined by counting (as best we could) the number of cells in an aliquot of the suspension culture. The cell cultures employed in this particular experiment were derived from a haploid plant that had been produced by another culture (Nitsch et al., Science, 163, 85–87 (1969)). From an initial population of $2.7 \times 10^6$ cells 54 resistant cell lines were isolated. This number represents only those cell lines that continued to exhibit resistance during a second passage on medium supplemented with 500 μM picloram. If it is assumed that all of these resistant cell lines resulted from independent mutations and that the contribution of the mutation rate is negligible, a spontaneous mutation frequency of $2 \times 10^{-5}$ can be calculated. Of course this frequency may represent the sum of the mutation frequencies for more than one genetic locus.

Genetic characterization of mutants: In the first plating of cell cultures derived from a diploid plant on medium containing 500 μM picloram 7 resistant cell lines (CL1-7) were isolated. The characterization of these cell lines exemplifies some of the difficulties encountered in plant cell genetics research. More than ten plants were regenerated from each of six resistant cell lines, but no plants could be regenerated from CL4. Callus cultures initiated from leaves of regenerated plants were tested for resistance to growth inhibition on medium containing 500 μM picloram. Callus derived from plants regenerated from five cell lines continued to exhibit herbicide resistance. Despite the fact that CL3 was stably resistant to picloram, even following several passages in its absence, resistance was not expressed by callus cultures obtained from ten plants regenerated from this cell line.

Since cell cultures derived from diploid plants were used in the initial mutant isolation experiment, regenerated plants would be expected to be heterozygous for a dominant allele. These alleles have been assigned the general symbol PmR (for picloram resistance) followed by the number of the originally isolated resistant cell line. For the sake of clarity it became necessary to adopt this notation even though it is not yet known if the mutations arose independently or if more than a single gene is involved. Thus, putatively heterozygous diploid plants regenerated from CL1 are designated PmR1/+.

Regenerated plants that gave rise to resistant callus were selfed and backcrossed. The segregation of resistance and sensitivity among the progeny was determined by plating surface-sterilized seed on medium supplemented with 100 μM picloram. No resistance was detected among seed produced by the self-fertilization of PmR5/+. However, germination of seed produced by crosses of PmR1/+, PmR2/+, PmR6/+, and PmR7/+ showed some degree of resistance to picloram. The numbers of resistant and sensitive progeny resulting from these crosses are presented in Table 2. These data are consistent with the ratios 3 resistant:1 sensitive and 1 resistant:1 sensitive that are expected from self and backcrosses, respectively, of a heterozygous individual in the case where resistance is conferred by a dominant allele of a single nuclear gene.

In platings on a higher picloram concentration (500 μM) of seed produced from crosses of PmR6/+, two distinct degrees of resistance to picloram were observed. In seedlings of one class (resistant) root and cotyledon development was affected less by picloram than in those of the other (intermediate) class. In one plating of 242 seed 64 proved resistant, 117 intermediate, and 61 sensitive. From these results it is evident that PmR6 is not completely dominant to the normal allele.

No resistant progeny were produced by a plant regenerated from a normal callus culture that had not been selected for resistance to picloram (Table 2). Therefore, it is evident that resistance among seed of

TABLE 1

Growth response to picloram of callus derived from F₁ isolates produced by selfing of PmR1/+.

| Picloram conc. (μm) | Normal (+/+) Final fresh wt. (mg) | % of control | N | Isolate 18(+/+) Final fresh wt. (mg) | % of control | N | Isolate 3 (PmR1/+) Final fresh wt. (mg) | % of control | N | Isolate 4 (PmR1/PmR1) Final fresh wt. (mg) | % of control | N | Isolate 11 (PmR1/PmR1) Final fresh wt. (mg) | % of control | N |
|---|---|---|---|---|---|---|---|---|---|---|---|---|---|---|---|
| 0 | 1471 ± 68 | 100 | 5 | 1295 ± 54 | 100 | 7 | 2301 ± 388 | 100 | 13 | 1381 ± 63 | 100 | 8 | 1160 ± 85 | 100 | 6 |
| 10 | 457 ± 32 | 31.1 | 5 | 271 ± 18 | 20.9 | 3 | 1894 ± 309 | 82.3 | 5 | 1289 ± 104 | 93.3 | 5 | — | | |
| 50 | 378 ± 27 | 25.7 | 4 | 246 ± 7 | 19.0 | 3 | 1944 ± 187 | 84.5 | 8 | 1224 ± 111 | 88.6 | 10 | 1094 ± 80 | 94.3 | 6 |
| 100 | 335 ± 20 | 22.8 | 5 | 232 ± 15 | 17.9 | 3 | 1494 ± 166 | 64.9 | 8 | 1276 ± 89 | 92.4 | 10 | — | | |
| 200 | 266 ± 17 | 18.1 | 3 | 207 ± 16 | 16.0 | 5 | 1702 ± 166 | 74.0 | 11 | 1554 ± 71 | 112.5 | 6 | 881 ± 121 | 76.0 | 6 |
| 500 | 219 ± 10 | 14.9 | 5 | 161 ± 14 | 12.4 | 5 | 1677 ± 113 | 72.9 | 6 | 1134 ± 121 | 82.1 | 5 | — | | |
| 1000 | 48 ± 2 | 3.2 | 5 | 48 ± 4 | 3.7 | 4 | 495 ± 114 | 21.5 | 7 | 464 ± 44 | 33.6 | 9 | 341 ± 69 | 29.4 | 4 |

Petri dishes were inoculated with approximately 50 mg. callus. After 14 days at 25±1° C. cultures were washed with distilled water and weighed. Numbers given are means and standard deviations of means (in mg) of N cultures. The relative response to picloram of each cell line is calculated as percent of growth (mean final fresh weight) in the absence of picloram.

PmR/+ plants does not result merely from passage through culture, but is a consequence of a rare event for which selection is necessary.

$F_1$ progeny produced by selfing PmR1/+ were self-fertilized and the seed were plated on selective medium to determine the $F_2$ segregation patterns. The results in Table 3 demonstrate that of 22 $F_1$ plants 5 were homozygous mutant (PmR1/PmR1), 6 were homozygous normal (+/+), and 11 were heterozygous (PmR1/+). The perfect fit of the composition of the $F_1$ to the theoretical pattern 1:2:1 confirms that the original regenerated plant was heterozygous for a dominant

TABLE 2

Segregation among progeny derived from crosses of plants regenerated from several picloram-resistant cell lines.

| | Number of individuals | | |
|---|---|---|---|
| Cross | Resistant Observed (Expected) | Sensitive Observed (Expected) | P |
| normal (from seed) selfed | 0 | 503 | |
| normal (from callus) selfed | 0 | 154 | |
| PmR1/+ selfed | 380 (380) | 127 (127) | 1.00 |
| PmR1/+ × normal | 27 (30) | 33 (30) | 0.44 |
| normal × PmR1/+ | 79 (82) | 85 (82) | 0.64 |
| PmR2/+ selfed | 308 (311) | 106 (105) | 0.79 |
| PmR6/+ selfed | 132 (130) | 41 (43) | 0.73 |
| PmR6/+ × normal | 67 (70) | 72 (70) | 0.66 |
| PmR7/+ selfed | 488 (490) | 165 (163) | 0.86 |

Surface-sterilized seed were plated on medium supplemented with 100 μM picloram. Plates were scored after 14d at 25°±1° C. resistance allele.

TABLE 3

$F_2$ progeny of random $F_1$ isolates obtained from self-fertilization of PmR1/+.

| | Number of $F_2$ individuals | | Presumed |
|---|---|---|---|
| $F_1$ isolate | Resistant | Sensitive | genotype |
| 1 | 405 | 126 | PmR1/+ |
| 2 | 186 | 71 | PmR1/+ |
| 3 | 358 | 134 | PmR1/+ |
| 4 | 330 | 0 | PmR1/PmR1 |
| 5 | 0 | 118 | +/+ |
| 6 | 213 | 71 | PmR1/+ |
| 7 | 0 | 247 | +/+ |
| 8 | 0 | 312 | +/+ |
| 9 | 0 | 324 | +/+ |
| 10 | 146 | 0 | PmR1/PmR1 |
| 11 | 408 | 0 | PmR1/PmR1 |
| 12 | 461 | 0 | PmR1/PmR1 |
| 13 | 418 | 155 | PmR1/+ |
| 14 | 0 | 316 | +/+ |
| 15 | 347 | 118 | PmR1/+ |
| 16 | 198 | 79 | PmR1/+ |
| 17 | 303 | 83 | PmR1/+ |
| 18 | 0 | 333 | +/+ |
| 19 | 343 | 151 | PmR1/+ |
| 20 | 222 | 0 | PmR1/PmR1 |
| 21 | 372 | 107 | PmR1/+ |
| 22 | 245 | 92 | PmR1/+ |

Furthermore, the recovery of the expected number of homozygous mutant individuals shows that, at least under laboratory conditions, the PmR1 mutation does not reduce viability.

Additional evidence for Mendelian inheritance is provided by the results of plating on selective medium seed obtained from selfing several plants produced by backcrosses. These experiments demonstrated that both heterozygous and homozygous normal individuals were produced in the crosses +/+ ×PmR1/+ (4 +/+ and 1 PmR1/+) and PmR6/+ ×+/+(4 +/+ and 2 PmR6/+).

Since plant cells accumulate chromosomal abnormalities in culture it is desirable to determine the chromosome number of plants regenerated from selected cell lines (Sunderland in "Plant Tissue and Cell Culture," ed. Street, Univ. of Calif. Press Berkeley Calif. pp. 161-190 (1973); Sacristan, Chromosoma, 33, 273-283 (1971)). However, in as much as plants regenerated from cell lines that have not been cloned may be chimeral, chromosomes of $F_1$ rather than of regenerated plants were counted. A normal diploid complement (2n=48) was observed in metaphase plates in corolla tissue prepared from two heterozygous $F_1$ progeny (Isolates 17 and 22) of PmR1/+.

Growth tests: The degree of resistance conferred by the PmR1 allele was examined by means of growth tests of callus cultures derived from $F_1$ plants. The genotypes of these plants were determined from segregation patterns of progeny seed plated on picloram-supplemented medium (Table 3). A callus culture produced from a normal plant grown from seed (not regenerated from culture or involved in crosses with mutants) also was included in these experiments. It is clear from the final fresh weight of cultures grown in the absence of picloram that the PmR1 mutation has no deleterious effect on the growth rate (Table 1). It also is evident that resistance to growth inhibition expressed by derivative callus cultures corresponds to resistance to inhibition of seed germination. That is, resistance to picloram was exhibited by callus cultures initiated from those plants that produced resistant seed (Isolates 3, 4, and 11) and not by those that produced sensitive seed (normal and Isolate 18).

The growth response to increasing picloram concentrations of callus obtained from a normal $F_1$ segregant (Isolate 18) is nearly identical to that of callus obtained from a normal seed-derived plant. Growth of both callus cultures is inhibited by 70% or more by only 10 μM picloram and completely by 1 mM. In contrast, severe growth inhibition of cultures obtained from mutant plants is not observed at picloram concentrations below 1 mM. Growth of callus derived from one homozygous mutant plant (Isolate 4) appears more resistant to picloram than does that of callus derived from a heterozygous plant (Isolate 3). However, the response of callus cultures obtained from another homozygous mutant segregant (Isolate 11) is more similar to the response of cultures derived from Isolate 3 than to that of cultures derived from Isolate 4. These results suggest that the growth response of these callus cultures to picloram may not be conditioned solely by the PmR1 allele and that the parent plant from which these segregants were obtained could have been heterozygous for alleles of other loci that also influenced the degree of picloram-resistance expressed in culture. From these data it appears that PmR1 is completely dominant over the normal allele. However, an additional possibility to be considered is that alleles of other loci (either present initially in that plant from which the original cell suspensions were derived or accumulated during maintenance of callus in culture) can modify the effect of PmR1 and that these also were segregating in the cross.

In the present study cell lines of *N. tabacum* were selected for resistance to the herbicide picloram and regenerated plants were characterized genetically. Of seven resistant cell lines initially isolated, only four gave rise to plants in which resistance proved stable and heritable. Plants could not be regenerated from one cell line. A second cell line, although stably resistant in culture even following many passages in the absence of picloram, gave rise to plants from which only sensitive callus cultures could be recovered. This result demonstrates that stability of a variant phenotype in culture in the absence of selection is not an adequate criterion for defining the genetic basis for the altered phenotype and indeed may not distinguish between genetic and epigenetic events.

Resistant callus cultures were recovered from plants regenerated from a third cell line (CL5). However, germination of seed from these plants was not resistant to the herbicide.

In the four cases in which picloram-resistance was transmitted across generations, three (PmR1, PmR2, and PmR7) behaved as dominant alleles and one (PmR6) as a semidominant allele of single nuclear gene(s). In one case (PmR1) the complete dominance of the resistance phenotype was confirmed by growth tests of callus cultures derived from plants of the three different genotypes segregating in the $F_1$ (+/+; PmR1/+; PmR1/PmR1). The recovery of only dominant and semidominant mutations was to be expected since the isolation of recessive mutations was essentially precluded by the use of diploid cells in the initial selection experiments. As the four resistant isolates were recovered from the same experiment it is possible that they did not originate independently. However, the semidominant phenotype of PmR6 shows that this mutation at least is probably distinct from the others even though it may be only a different allele of the same locus. Genetic crosses are being initiated as tests of allelism of the four mutants.

The results of the growth tests suggest that heterozygosity of plants regenerated from resistant cell lines may not be restricted to the PmR locus in question. Allelic forms of other genes that modify the PmR1-mediated resistance to growth inhibition by picloram also may have been segregating in these crosses.

Germination of seed of the four mutants is resistant to inhibition by 100 μM picloram. However, if seedlings are left in the presence of picloram they will not develop further and soon begin to deteriorate. In an initial attempt to detect expression of resistance in the plant normal (+/+) and PmR1/PmR1 aseptically-grown plantlets (approximately 5 cm high) were transferred to medium containing 50 μM picloram. The normal plants rapidly bleached and died whereas growth of the mutant plants was inhibited only slightly. After one month callus tissue formed from the stems of the mutant plants and then these plants began to degenerate.

I claim:

1. A method for the preparation of a relatively herbicide tolerant plant, selected from the group consisting of tobacco, rice, corn, potato, oats, alfalfa, carrot and sugar cane, which displays heritable increased tolerance to said herbicide, which method comprises:
    (a) tissue culturing, in the presence of a herbicide to which a parent plant is sensitive, and to which a tissue culture derived from said parent plant is also sensitive, tissue from said parent plant, said tissue culturing being conducted in the presence of an amount of said herbicide sufficient to kill at least 90% of the tissue initially present and
    (b) subjecting the surviving culture tissue or plants derived therefrom to a process which isolates plant tissue or plants which display heritable increased tolerance to said herbicide.

2. A method as in claim 1 wherein the amount of herbicide kills in excess of 99% of the plant tissue initially present.

3. A method as in claim 1 or 2 wherein the surviving cultured tissue is subjected to at least one additional culturing step in the presence of said herbicide.

4. A method as in claim 3 wherein each additional culturing step is conducted in the presence of an increased amount of said herbicide.

5. A method for the preparation of a relatively herbicide tolerant plant, selected from the group consisting of tobacco, rice, corn, potato, oats, alfalfa, carrot and sugar cane, which displays heritable increased tolerance to said herbicide, which method comprises:
    (a) tissue culturing, in the presence of a herbicide, selected from the group consisting of picloram, paraquat, 2,4-D, glyphosphate, alachlor, atrizine and amitrole, to which a parent plant is sensitive, and to which a tissue culture derived from said parent plant is also sensitive, tissue from said parent plant, said tissue culturing being conducted in the presence of an amount of said herbicide sufficient to kill at least 90% of the tissue initially present and
    (b) subjecting the surviving culture tissue or plants derived therefrom to a process which isolates plant tissue or plants which display heritable increased tolerance to said herbicide.

6. A method as in claim 5 wherein the amount of herbicide kills in excess of 99% of the plant tissue initially present.

7. A method as in claim 5 or 6 wherein the surviving cultured tissue is subjected to at least one additional culturing step in the presence of said herbicide.

8. A method as in claim 7 wherein each additional culturing step is conducted in the presence of an increased amount of said herbicide.

9. A method as in claim 1 where the plant is tobacco.

10. A method as in claim 5 where the plant is tobacco.

11. A method as in claims 1, 5 or 10 where the culturing step is a suspension tissue culturing step.

* * * * *

UNITED STATES PATENT AND TRADEMARK OFFICE
CERTIFICATE OF CORRECTION

PATENT NO. : 4,443,971
DATED : April 24, 1984
INVENTOR(S) : Roy S. Chaleff

It is certified that error appears in the above-identified patent and that said Letters Patent is hereby corrected as shown below:

In Claim 5, line 8, delete "atrizine" and insert

--atrazine--.

Signed and Sealed this

Twelfth Day of March 1985

[SEAL]

Attest:

DONALD J. QUIGG

Attesting Officer   Acting Commissioner of Patents and Trademarks